US012234089B2

(12) United States Patent
LaTorre et al.

(10) Patent No.: US 12,234,089 B2
(45) Date of Patent: Feb. 25, 2025

(54) MEDICAL WASTE CONTAINER TRANSPORT DEVICE AND SYSTEM

(71) Applicant: Stericycle, Inc., Bannockburn, IL (US)

(72) Inventors: Matthew S. LaTorre, Smithtown, NY (US); William Riess, Hatfield, PA (US)

(73) Assignee: Stericycle, Inc., Bannockburn, IL (US)

( * ) Notice: Subject to any disclaimer, the term of this patent is extended or adjusted under 35 U.S.C. 154(b) by 169 days.

(21) Appl. No.: 17/973,315

(22) Filed: Oct. 25, 2022

(65) Prior Publication Data
US 2023/0135147 A1 May 4, 2023

Related U.S. Application Data

(60) Provisional application No. 63/274,291, filed on Nov. 1, 2021.

(51) Int. Cl.
*B65F 1/14* (2006.01)
*A61B 50/36* (2016.01)
*B65F 1/16* (2006.01)

(52) U.S. Cl.
CPC .......... *B65F 1/1452* (2013.01); *A61B 50/362* (2016.02); *B65F 1/16* (2013.01)

(58) Field of Classification Search
CPC ...... B65F 1/1452; B65F 1/1457; B65F 1/141; B65F 1/1415; B65F 1/1421; B65F 1/1468; B65F 1/16
See application file for complete search history.

(56) References Cited

U.S. PATENT DOCUMENTS

| | | | |
|---|---|---|---|
| 4,913,309 A | 4/1990 | Fink | |
| 5,038,929 A | 8/1991 | Kubofcik | |
| 5,048,712 A * | 9/1991 | Wolters | B65F 1/163 |
| | | | 220/908 |
| 5,291,746 A | 3/1994 | Abbott | |
| 7,063,212 B2 | 6/2006 | Ordonez | |
| 7,114,629 B2 * | 10/2006 | Panek, Jr. | A61B 50/36 |
| | | | 220/908 |
| 7,159,714 B2 | 1/2007 | Wilkinson et al. | |

(Continued)

FOREIGN PATENT DOCUMENTS

DE 4136171 A1 5/1993

OTHER PUBLICATIONS

AliMed,Workstation Phlebotomy Cart & Accesories, (alimed.com)<https://www.alimed.com/phlebotomy-workstation-cart-and-accessories.html?pid=82155&gclid=EAlalQobChMI08yEqaHH8gIVOf3jBx0LIgOIEAQYESABEgLzhPD_BwE>, last visited on Aug. 23, 2021, Copyrighted in 2022, 3 page screenshots.

*Primary Examiner* — Javier A Pagan
(74) *Attorney, Agent, or Firm* — Michael Best & Friedrich LLP

(57) ABSTRACT

A transport device to removably receive a medical waste container for transport of the medical waste container includes a body having a base wall with at least one opening for receiving a medical waste container. A portion of the base wall defining the at least one opening is configured to engage and completely surround an exterior of the medical waste container. The body further includes a side wall extending from the base wall, the base wall and side wall together defining a cavity. A cover is movably coupled to the side wall and is movable between a closed position, in which the cover cooperates with the side wall to close a top of the cavity, and an open position, in which the cavity is open at the top.

22 Claims, 12 Drawing Sheets

(56) References Cited

U.S. PATENT DOCUMENTS

| | | |
|---|---|---|
| 7,513,363 B2 | 4/2009 | Brown et al. |
| 7,562,025 B2 | 7/2009 | Mallett et al. |
| 7,784,167 B2 | 8/2010 | Panek, Jr. |
| 8,201,704 B2 | 6/2012 | Finnestad et al. |
| 8,560,460 B2 | 10/2013 | Mallett et al. |
| 8,613,366 B2 | 12/2013 | Finnestad et al. |
| 8,695,834 B2 | 4/2014 | Panek, Jr. |
| 8,868,434 B2 | 10/2014 | Mallett |
| 9,044,377 B2 | 6/2015 | Maness |
| 9,456,954 B2 | 10/2016 | Maness |
| 9,566,128 B2 | 2/2017 | Erickson et al. |
| 10,086,416 B2 | 10/2018 | Maness |
| 10,358,256 B2 * | 7/2019 | Travis ............... B62B 1/12 |
| 10,435,240 B1 * | 10/2019 | Stroop ............ B65F 1/1415 |
| 10,646,907 B2 | 5/2020 | Maness |
| 2008/0156666 A1 | 7/2008 | Panek |
| 2009/0166373 A1 | 7/2009 | Brown et al. |
| 2015/0034534 A1 | 2/2015 | Mallett |
| 2016/0302877 A1 | 10/2016 | Schwaegerle et al. |
| 2017/0158427 A1 * | 6/2017 | Dafoe ............... B62B 3/02 |
| 2018/0079580 A1 | 3/2018 | Midali |
| 2019/0256266 A1 | 8/2019 | Komann |
| 2020/0246848 A1 | 8/2020 | Maness |

\* cited by examiner

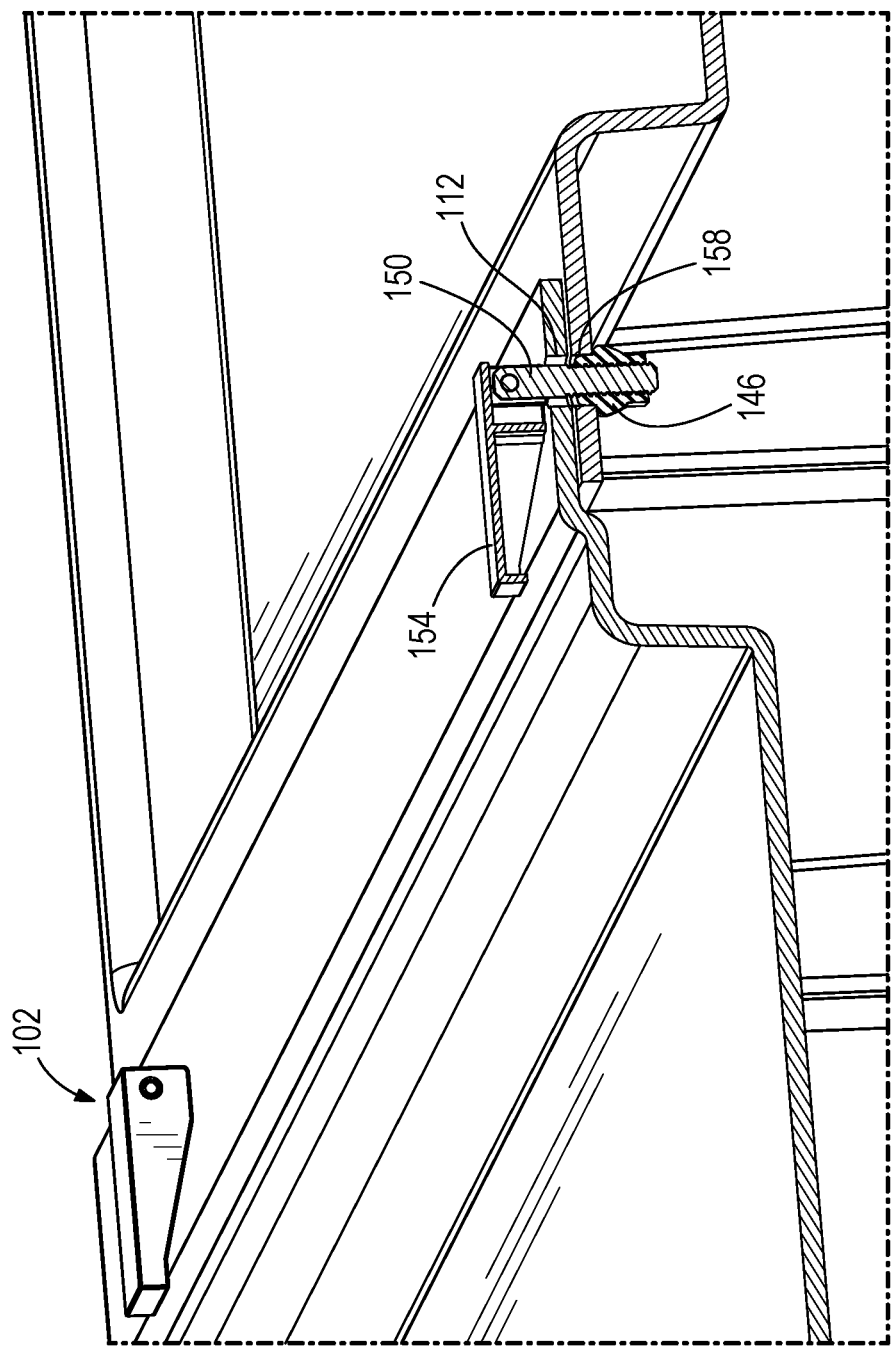

MEDICAL WASTE CONTAINER TRANSPORT DEVICE AND SYSTEM

RELATED APPLICATIONS

This application claims the benefit of U.S. Provisional Patent Application No. 63/274,291 filed Nov. 1, 2021, the entire content of which is hereby incorporated by reference herein.

BACKGROUND

The invention relates to devices and systems for transporting filled medical waste (e.g., sharps) containers. Current devices and systems include single-use bags and boxes. Preparation, loading, and disposal of these current products can be cumbersome and time-consuming. There is also waste generated from the single-use packaging in that the bags, closure tape, and boxes must be destroyed and/or recycled.

SUMMARY

In one aspect, the disclosure provides a transport device configured to removably receive a medical waste container for transport of the medical waste container. The transport device includes a body having a base wall with at least one opening for receiving a medical waste container. A portion of the base wall that defines the at least one opening is configured to engage and completely surround an exterior of the medical waste container. The body further includes a side wall extending from the base wall, the base wall and side wall together defining a cavity. A cover is movably coupled to the side wall and is movable between a closed position, in which the cover cooperates with the side wall to close a top of the cavity, and an open position, in which the cavity is open at the top.

In another aspect, the disclosure provides a method of using the transport device and includes placing the transport device on a support surface with the base wall on the support surface, moving the cover to the open position such that the cavity is open at the top, placing the medical waste container through the open top of the cavity into the cavity so that a bottom of the medical waste container is positioned in the at least one opening and on the support surface, moving the transport device relative to the medical waste container toward a top of the medical waste container until an exterior of the medical waste container engages a portion of the base wall defining the at least one opening, and moving the cover to the closed position so that an upper end of the medical waste container is enclosed within the closed cavity of the transport device.

BRIEF DESCRIPTION OF THE DRAWINGS

FIG. 3D is a partial section view illustrating the lock.

DETAILED DESCRIPTION

Figure 1:
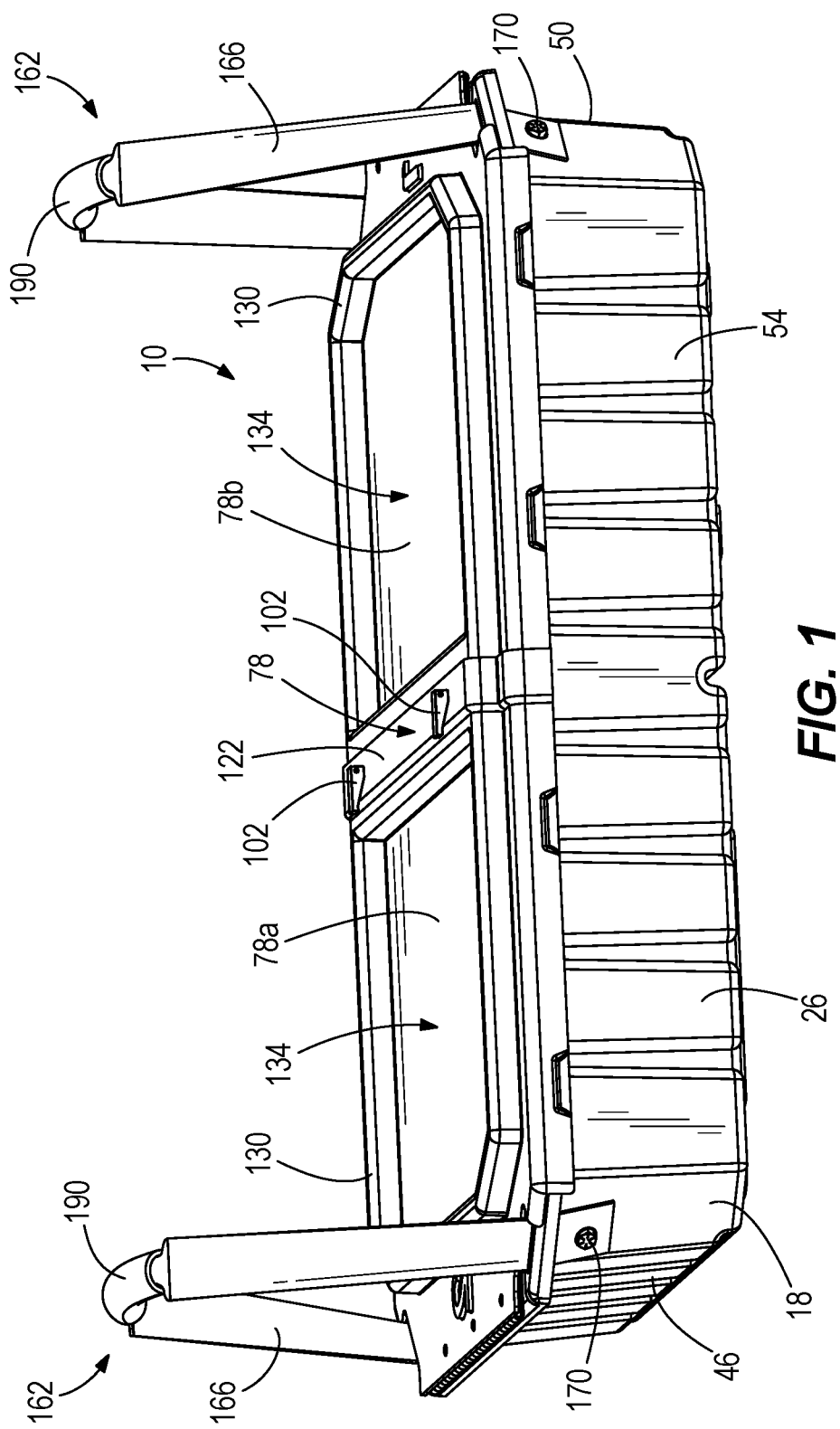
FIG. 1 is a perspective view of a transport device for use in transporting medical waste containers according to one embodiment of the present disclosure.

Before any embodiments of the present invention are explained in detail, it is to be understood that the invention is not limited in its application to the details of construction and the arrangement of components set forth in the following description or illustrated in the following drawings. Use of relative terms such as "upward," "downward," "up," "down," "top," and "bottom," as well as derivatives of such terms (e.g., "downwardly" and "upwardly") should be construed to refer to an exemplary orientation as then described or as shown in the drawing under discussion. These relative terms are for convenience of description and do not require that the apparatus be constructed or operated in a particular orientation. The invention is capable of other embodiments and of being practiced or of being carried out in various ways.

Sharp medical devices are used on patients in invasive procedures, necessitating strict requirements for post-use handling and disposal. Used medical devices are unclean, often having been in contact with blood or other bodily fluids of a patient, but are still sharp. Indeed, many of these medical devices have a point or edge sharp enough to penetrate containers designated for common waste. Single-use medical devices are thus commonly disposed after use in a "sharps" container. Sharps containers are well known to those who work in medical care facilities and are intended to be used to collect potentially dangerous, used sharp medical devices that are capable of cutting or penetrating skin or penetrating a conventional waste package container. Sharps containers may contain used syringes, needles, and broken glass. These containers are periodically picked up from a medical care facility by a regulated waste collector and transported to an off-site disposal location. In some cases, the medical care facility may purchase sharps containers outright and, when filled, contract a service to remove the permanently sealed containers, which are then completely destroyed (e.g., via comminution and/or incineration) along with the contents thereof. In other cases, medical care facilities rent reusable sharps containers. When these containers are filled, they are transported to a disposal site where they are opened, emptied, and then cleaned and disinfected before being returned to the same or other medical care facility for reuse.

Figure 2:
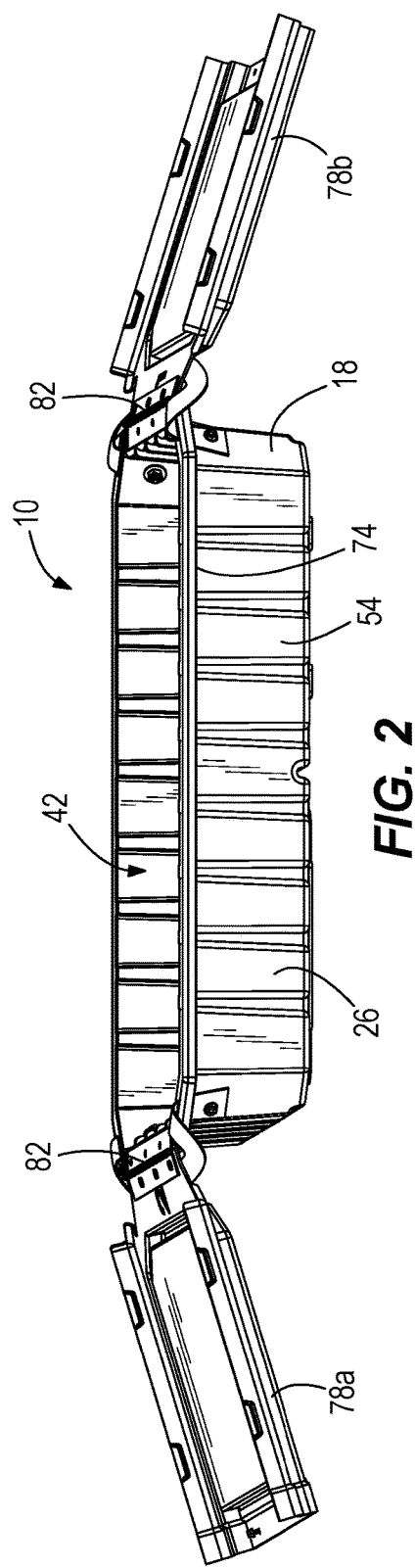
FIG. 2 is a side perspective view of the transport device of FIG. 1, with the cover in the open position.
Figure 3:
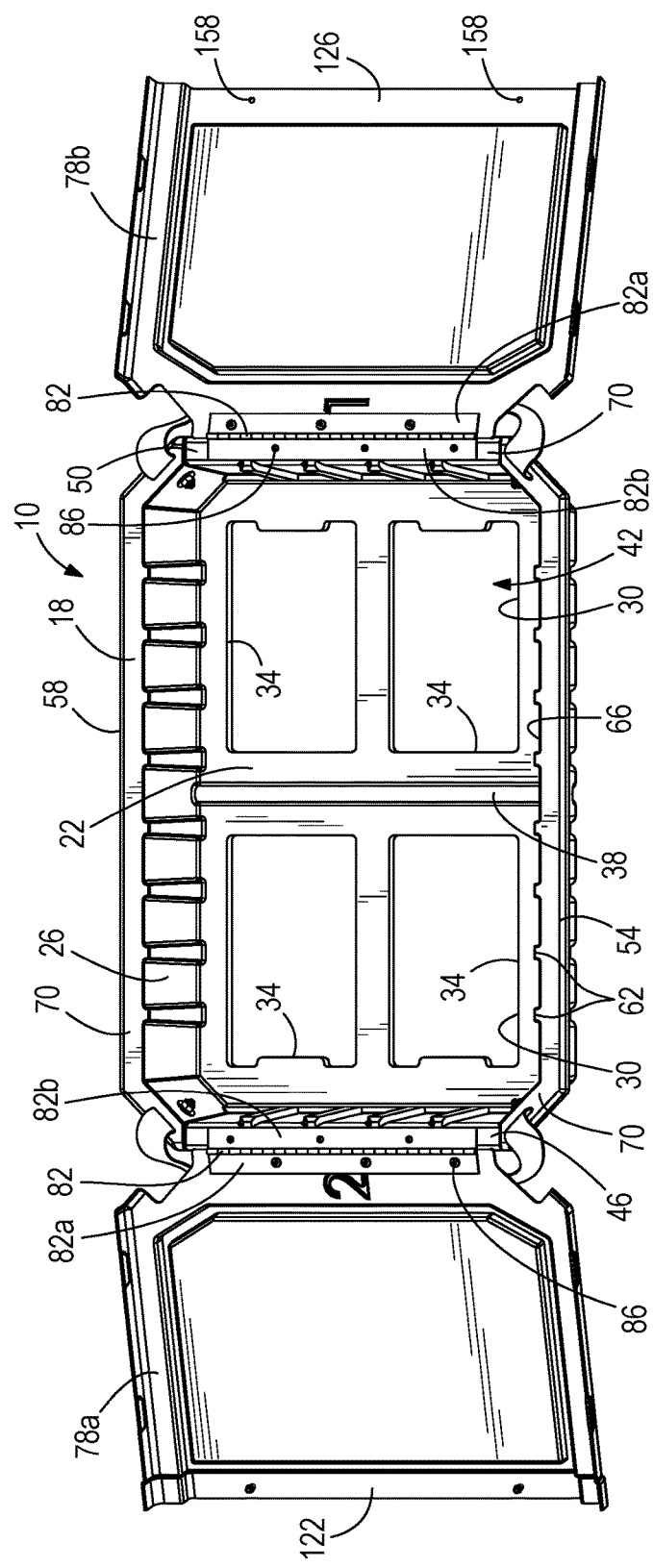
FIG. 3 is a top perspective view of the transport device of FIG. 1, with the cover in the open position.
Figure 3A:
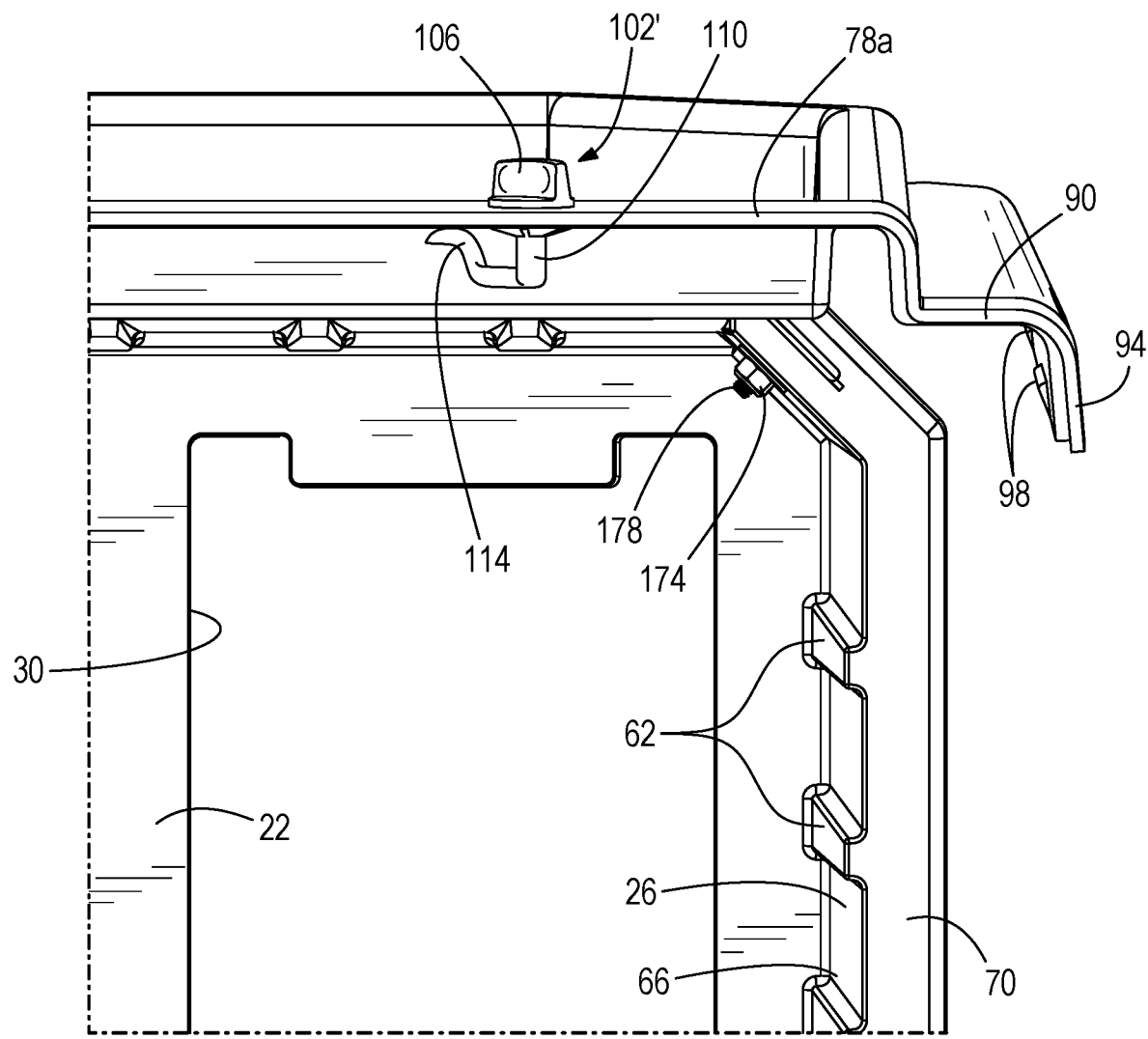
FIG. 3A is an enlarged partial end view of one side of the cover in an open position looking downward at the free end of the one side of the cover and into the open transport cavity, and illustrates an exemplary embodiment of a lock.
Figure 3B:
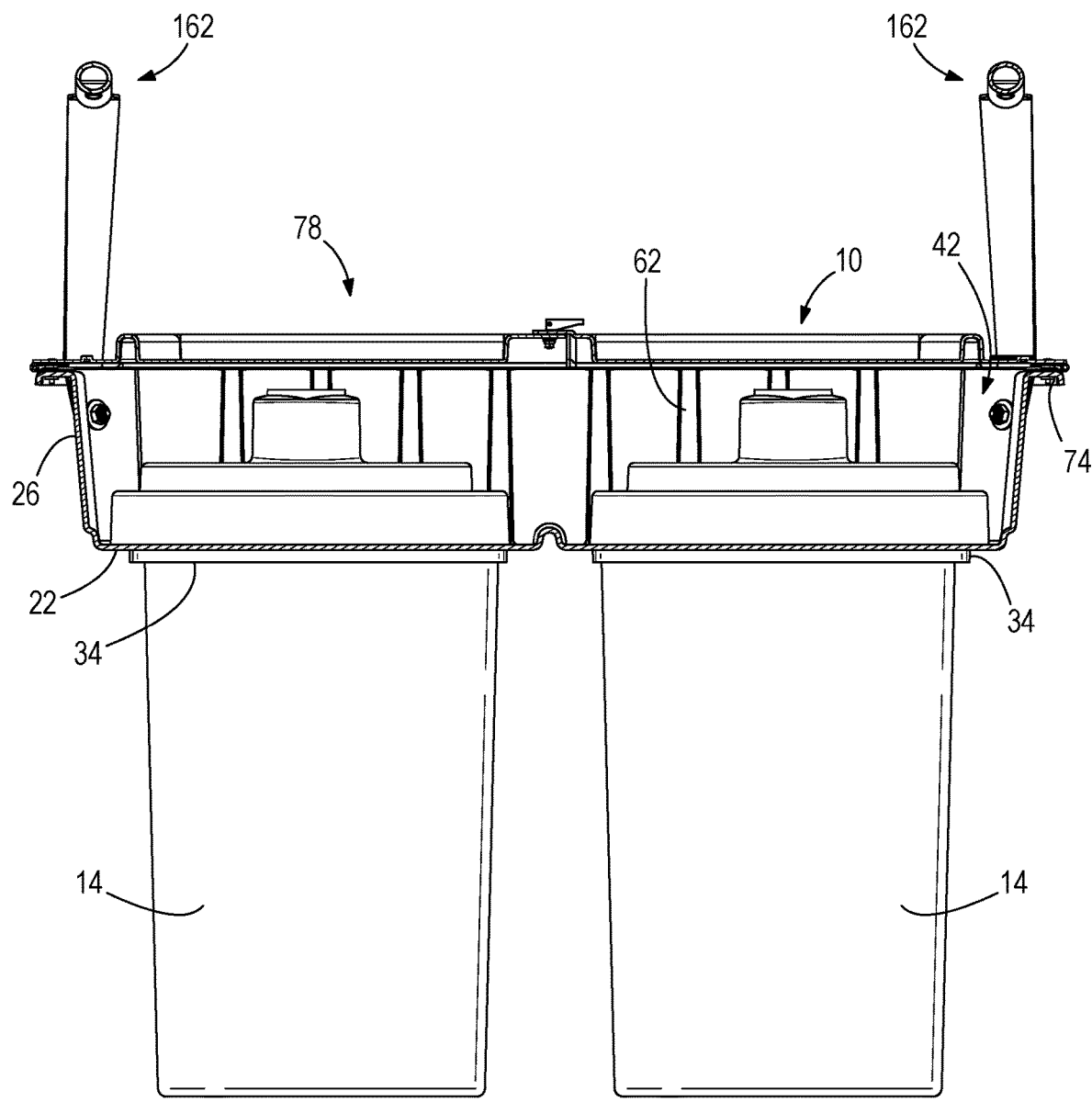
FIG. 3B is a section view showing two containers supported within the transport device of FIG. 1.

FIGS. 1-3D illustrate a transport device 10 designed to securely contain one or more (e.g., four) medical waste containers or sharps containers 14 (see FIG. 3B). The illustrated device 10 can be made from a durable plastic material and is thus re-usable to transport filled sharp containers 14 from the medical care facilities to an off-site disposal facility. The device includes a body 18 having a base wall 22 (see FIG. 3) and a side wall 26 extending from the base wall 22 in an upward direction as shown in FIGS. 1-3 and 3B. The base wall 22, which in the illustrated orientation defines the bottom of the body 18, includes at least one opening 30 for receiving a sharps container 14 as will be described further below. As illustrated in FIGS. 1-3, the base wall 22 includes four openings 30 configured to each support a sharps container 14, such that the transport device 10 can contain and support a total of four sharps containers 14 at one time.

Figure 6:
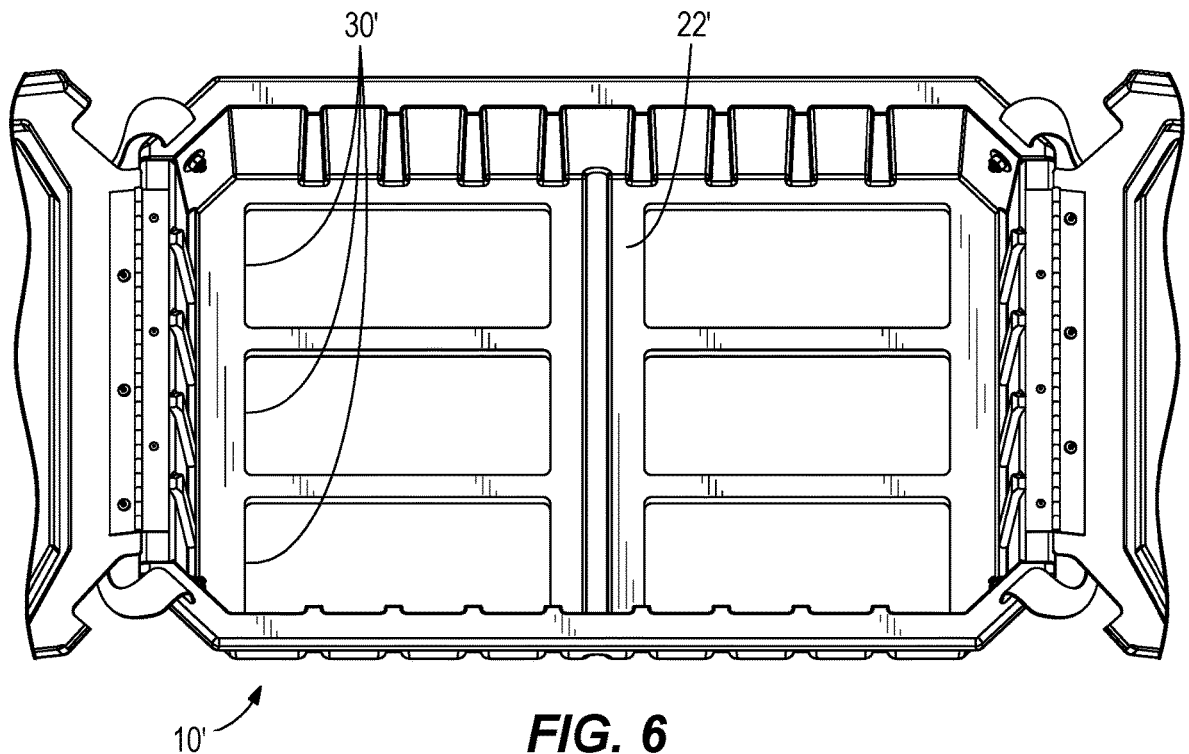
FIG. 6 is a perspective view of an alternative transport device having six openings for receiving six medical waste containers.
Figure 7:
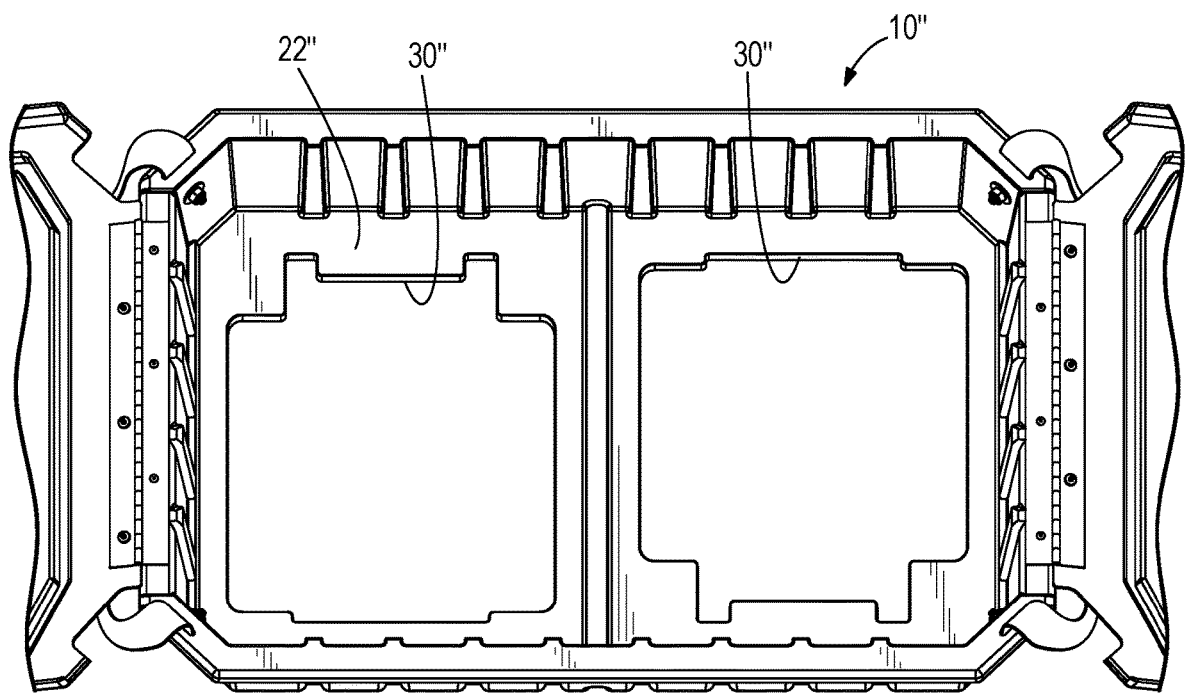
FIG. 7 is a perspective view of an alternative transport device having two openings for receiving two medical waste containers.

The openings 30 can be formed into the base wall 22 during a forming (e.g., molding) process of the body 18, or alternatively can be die cut into the base wall 22 after the body 18 is initially formed. If formed during molding, different mold inserts can be substituted into the mold to create the desired configuration of openings. By using the die-cutting process, a single mold for the body 18 can be used, and multiple opening configurations can be selectively cut/punched/formed after the molding operation to obtain the desired opening configuration depending upon the size and shape of the various sharps containers 14 to be transported. For example, FIG. 6 illustrates an alternative transport device 10' that includes six openings 30' in the base wall 22' and FIG. 7 illustrates another alternative transport device 10" that includes two openings 30" in the base wall 22". Other than the different number and configurations of openings 30, 30', 30", the transport devices 10, 10', and 10" are identical.

Referring to FIGS. 3 and 3B, each opening 30 is defined by a portion of the base wall 22 that defines a perimeter or outer boundary of the opening 30. Specifically, each opening 30 is defined by an edge or boundary portion 34 of the base wall 22 that circumscribes the opening 30. The boundary portions 34 can have a height or thickness corresponding to the thickness of the base wall 22 (as would be the case where the openings 30 are formed by die cutting the base wall 22), or can be thicker than a remainder of the base wall 22 if desired (as could be the case where the openings 30 are formed during the molding process-see FIG. 3B). The geometry of the boundary portions 34 is designed to substantially correspond to the geometry of an exterior surface of the specific sharps container 14 to be received in the opening 30 such that, when the container 14 is inserted into the opening 30, the device 10 can be manipulated relative to the container 14 (as will be described below) so that the much or all of the boundary portion 34 engages the exterior surface of the container 14. The openings 30 are configured so that when the containers 14 are engaged with the boundary portions 34, the containers 14 will fit snugly therein and are substantially constrained against movement in any direction lying in the same plane as the base wall 22 (i.e., horizontally, that is, to the right or left or into or out of the page in FIG. 2). In other words, each boundary portion 34 completely surrounds the container 14 on all sides so that the container cannot move horizontally in any direction.

The containers 14 are typically tapered from a narrower dimension at the lower end to a wider dimension at the upper end. With that in mind, the boundary portion 34 can be configured so that engagement between the boundary portion 34 and the exterior of the container 14 will occur at some desired location between the lower and upper ends of the container 14. Thus, with reference to FIGS. 3B and 5, the engagement between the boundary portion 34 and the exterior of the container 14 will act to limit movement of the container 14 in a downward direction (in the orientation shown in FIG. 5) relative to the base wall 22. In this manner, the boundary portion 34 in conjunction with the configuration of the container 14 dictates how much of the container 14 extends downwardly from the bottom of the base wall 22 and provides a limit to the movement of the container 14 relative to the device 10 in the downward direction when the container 14 is received in the opening 30.

In the illustrated embodiment, the boundary portions 34 grip the tapered exterior walls of the respective containers 14 such that the frictional engagement between the boundary portions 34 and the exterior walls of the containers 14 is the limiting feature that prevents further downward motion of the containers 14 relative to the base wall 22. While it may appear in FIG. 3B that the lids of the containers 14 could be acting as stops or limiting features, this is not the case in the illustrated embodiment. However, in other embodiments, the exterior walls of the containers 14 could include shoulders, bosses, projections, or other features that could act as limiting structural features in engagement with the base wall 22. In further embodiments, a portion of the container lids could also act as limiting structural features in engagement with the base wall 22.

The base wall 22 may further include one or more ribs 38 (see FIG. 3) configured to add strength and rigidity to the base wall 22.

Figure 4:
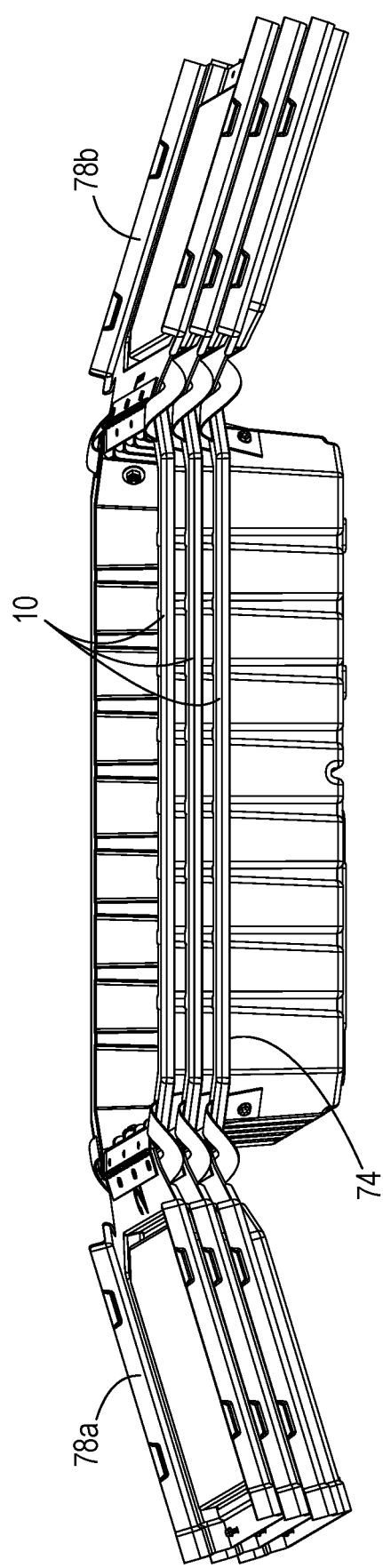
FIG. 4 is a perspective view illustrating a plurality of transport devices nested together.

The illustrated side wall 26 extends upwardly from the base wall 22 about the periphery of the base wall 22 to define a cavity 42 within the confines of the side wall 26 and in the space above the base wall 22. The illustrated side wall 26 is rectangular in shape having a first side wall portion 46, a second side wall portion 50 opposite to the first side wall portion 46 across the cavity 42, a third side wall portion 54, and a fourth side wall portion 58 opposite to the third side wall portion 54 across the cavity 42. The illustrated side wall 26 is formed with a draft angle (e.g., 2-5 degrees) such that the cavity 42 tapers from a narrower dimension adjacent the base wall 22 to a wider dimension adjacent the top or upper end of the cavity 42. In addition to facilitating molding, the draft angle enables multiple transport devices 10 to be nested within one another as shown in FIG. 4 for efficient storage and transport. The side wall 26 may also include ribbing 62 on an interior surface 66 of the side wall 26 defining the cavity 42. This ribbing 62 can increase the strength and rigidity of the side wall 26.

In the illustrated embodiment, the upper end of the side wall 26 (i.e., the end spaced from the base wall 22) includes a flange or rim 70 that defines an uppermost edge of the side wall 26 and an uppermost edge of the cavity 42. A downwardly extending lip 74 (see FIGS. 2 and 3B) extends from an outermost periphery of the flange 70 back toward the base wall 22. The lip 74 provides strength and rigidity to the flange 70. Furthermore, the flange 70 and lip 74 are configured to engage with a cover arrangement of the transport device 10, as will be described further below.

The transport device 10 further includes a cover 78, which in the illustrated embodiment includes a first cover portion 78a and a second cover portion 78b. The first cover portion 78a is movably coupled to the side wall 26, and more specifically, is pivotably coupled to the first side wall portion 46. As illustrated, a hinge 82 has a first hinge half 82a coupled to the first cover portion 78a and a second hinge half 82b coupled to the flange 70 on the first side wall portion 46.

Fasteners 86 (e.g., rivets) can be used to secure the hinge halves 82a, 82b to each of the first cover portion 78a and the flange 70. Alternatively, the transport device 10 could be formed such that the first cover portion 78a is integrally formed with the first side wall portion 46 and joined thereto at a living hinge.

The second cover portion 78b is movably coupled to the side wall 26, and more specifically is pivotably coupled to the second side wall portion 50. As illustrated, a hinge 82 has a first hinge half 82a coupled to the second cover portion 78b and a second hinge half 82b coupled to the flange 70 on the second side wall portion 50. Fasteners 86 (e.g., rivets) can be used to secure the hinge halves 82a, 82b to each of the second cover portion 78b and the flange 70. Alternatively, the transport device 10 could be formed such that the second cover portion 78b is integrally formed with the first side wall portion 46 and joined thereto at a living hinge.

The first and second cover portions 78a, 78b can move or pivot between the closed position shown in FIGS. 1 and 3B and the open position shown in FIGS. 2 and 3. In the closed position, the cavity 42 is closed at its upper end by the first and second cover portions 78a, 78b. In the open position, the first and second cover portions 78a, 78b do not cover the cavity 42, but instead extend away from the body 18 in opposite directions. As seen in FIGS. 2, 3, and 4, when the first and second cover portions 78a, 78b are opened, they can extend at or beyond 180 degrees relative to the plane defined by the flange 70 so as to minimize the overall height of the transport device 10 when placed on the ground or on another support surface and when nested with other transport devices 10. The first and second cover portions 78a, 78b cooperate with one another to define a cover 78 that can completely close off the upper end of the cavity 42.

In alternative embodiments, the cover 78 could be formed as a single piece sized to close the entire upper end of the cavity 42. That single-piece cover could be hingedly connected to the side wall 26 in a similar manner as shown for each of the first and second cover portions 78a, 78b in the figures. In yet another alternative embodiment, the first and second cover portions 78a, 78b could be slidably coupled with the upper end of the side wall 26 to move between the open and closed positions. A single-piece cover could likewise be slidably coupled in this manner. In yet another alternative embodiment, a single-piece cover could be a separate part that could be movably coupled or uncoupled from the side wall 26 to close or open the top of the cavity 42.

FIG. 3A illustrates an enlarged partial end view of the first cover portion 78a. Each cover portion 78a, 78b includes an edge profile configured to mate with the flange 70 and the lip 74 along the respective third and fourth side wall portions 54, 58. As best seen in FIG. 3A, each edge profile includes flange-engaging portion 90 that is configured to engage the upper surface of the flange 70 when the cover portion 78a is in the closed position, and a skirt portion 94 extending downwardly from the flange-engaging portion 90. The skirt portion 94 is configured to engage with an outer surface of the lip 74 when the cover portion 78a is in the closed position. The skirt portion 94 includes a plurality of inwardly extending projections 98 configured to engage a distal end of the lip 74 to secure the cover portion 78a in the closed position. In other words, as the cover portion 78a moves to the closed position, the projections 98 abut and slide along the outwardly-facing surface of the lip 74 on the side wall 26. There is some interference in the dimensions between the lip 74 and the projections 98 such that there is a resilient deflection of the skirt portion 94 relative to the lip 74 until the projections 98 pass by the distal end of the lip 74 and then catch or latch underneath the distal end of the lip 74. This arrangement of the projections 98 catching in place under the distal end of the lip 74 helps to secure and releasably maintain the cover portions 78a, 78b in the closed position.

The illustrated cover 78 further includes one or more locks, latches, or securing devices 102 (hereinafter referred to as locks), which as shown in FIG. 3D, can take the form of an expanding pivot lock. The illustrated exemplary lock 102 in FIG. 3D is of a known arrangement. The lock 102 is positioned to remain secured to the first cover portion 78a, and includes an expandable bumper 146, a shaft 150 that is coupled at one end to the bumper 146, and a pivoting latch member 154. The pivoting latch member 154 is pivotally coupled to the end of the shaft 150 that is opposite to the end of the shaft 150 received in the bumper 146. The bumper 146 is in a collapsed or retracted state when the latch member 154 is pivoted to align axially with the shaft 150, and is in an expanded state when the latch member 154 is pivoted to be generally perpendicular to the shaft 150, as shown in FIG. 3D.

The lock 102 is coupled to the first cover portion 78a by pushing the bumper 146 through an aperture 112 in the first cover portion, which aperture 112 is smaller in diameter than the bumper 146 even in the collapsed state. Resilient deformation of the bumper 146 occurs to allow the bumper 146 to pass through the aperture 112. Once installed in this manner, the lock 102 should remain coupled with the first cover portion 78a. To close and secure the first and second cover portions 78a, 78b, the user closes the second cover portion 78b first. Next, the first cover portion 78a is closed, taking care to have the bumper 146 extend into and pass through an aperture 158 in the second cover portion 78b. Some manipulation of the lock 102 may be needed to align the bumper 146 with, and insert it into, the aperture 158 in the second cover portion 78b. To lock the covers closed, the latch member 154 is pivoted to an orientation that is generally perpendicular to the shaft 150 as seen in FIG. 3D. In this orientation, the bumper 146 expands to fill the aperture 158 and create an interference fit therewith. A portion of the expanded bumper 146 also extends through the aperture 158 and engages an underside of the second cover 78b. This locking arrangement secures or locks the first and second cover portions 78a, 78b together and therefore, in a locked, closed condition.

Other types of locks 102 can also be used. For example, as shown in FIG. 3A, the lock 102 can alternatively take the form of a rotatable lock or twist lock 102". A knob 106 is positioned on a top surface of the first cover portion 78a. A shaft portion 110 extends from the knob 106, through an aperture 112 (see FIG. 1) in the first cover portion 78a, and terminates at a latch portion 114. Rotation of the knob 106 by a user, rotates the shaft portion 110, and moves the latch portion 114 so that the latch portion 114 can rotate into engagement with an underside of the second cover portion 78b. With this lock 102', the second cover portion 78b can include notches or cutouts configured to receive the latch portion 114. This latching engagement secures or locks the first and second cover portions 78a, 78b together and therefore, in a locked, closed condition.

As shown in FIG. 1, in the illustrated embodiment, the first cover portion 78a at least partially overlies the second cover portion 78b when the cover portions 78a, 78b are in the closed position. The first cover portion 78a therefore includes an overlapping portion 122 that has a slightly larger overall dimension than the abutting underlapping portion 126 (see FIG. 3) of the second cover portion 78b. In other embodiments, different abutting and/or overlapping arrangements could be used between the first and second cover portions 78a, 78b.

Figure 8:
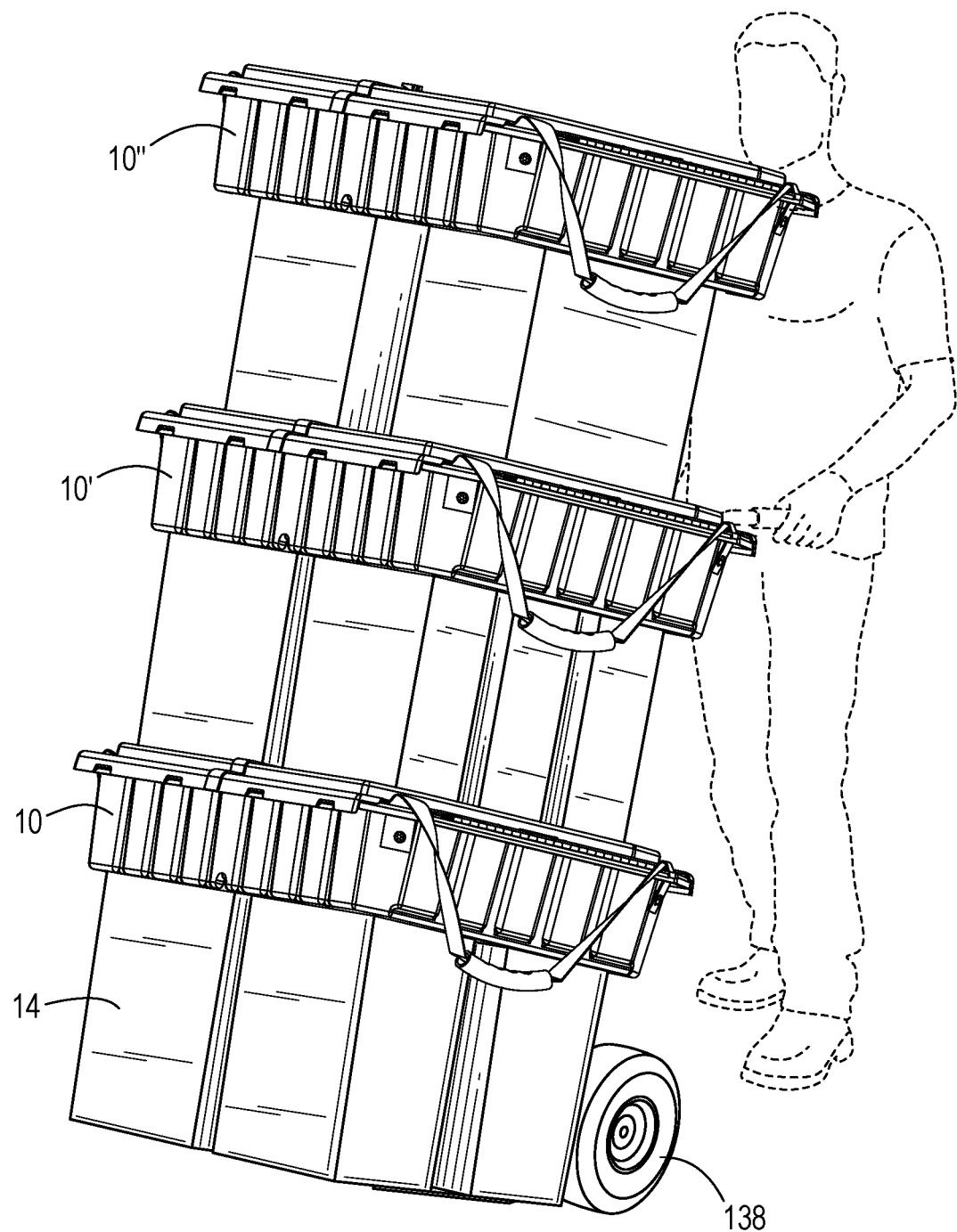
FIG. 8 is a perspective view showing multiple transport devices containing medical waste containers and stacked on a transport dolly.
Figure 9:
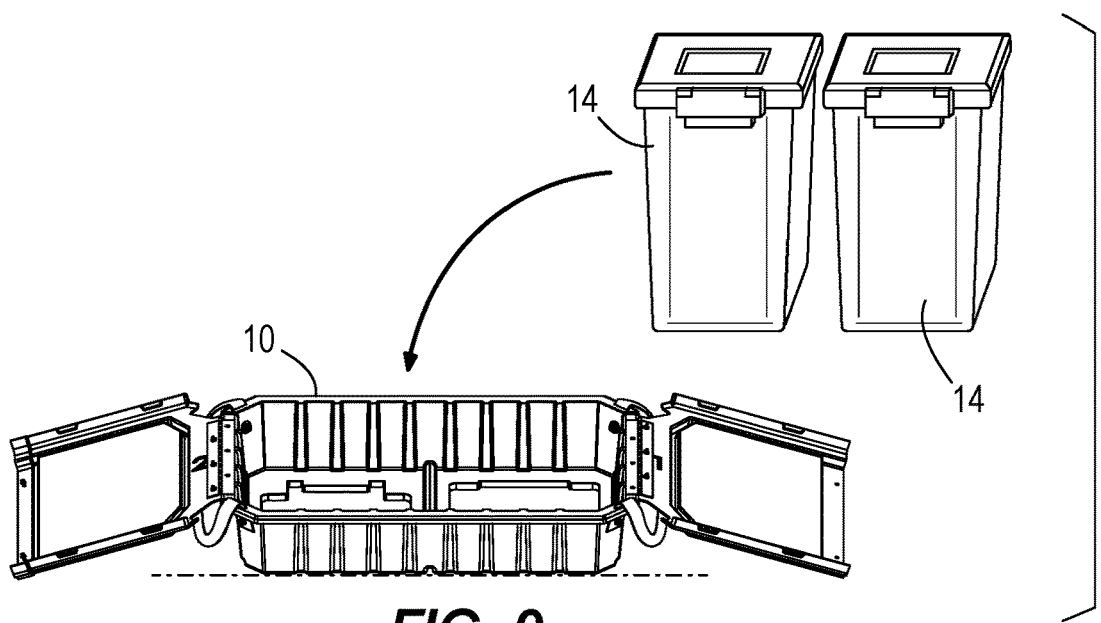
FIGS. 9-13 illustrate the method of loading the transport device of FIG. 1 with medical waste containers.
Figure 10:
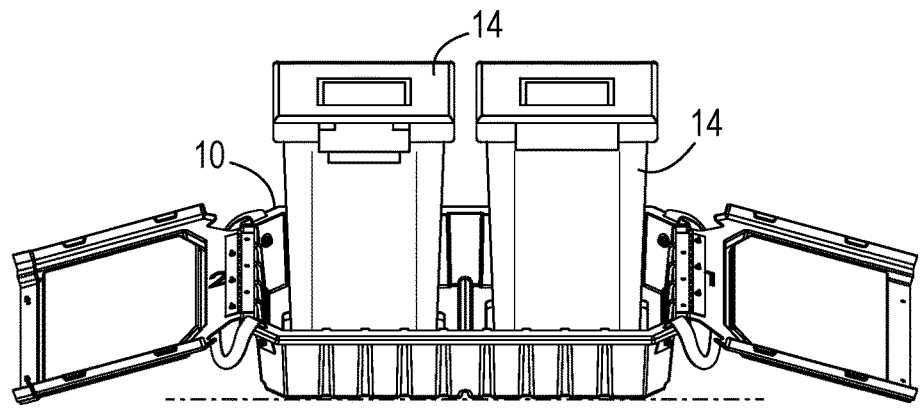

With continued reference to FIG. 1, the cover 78, and more specifically each of the first and second cover portions 78a, 78b, includes a rib 130 that defines a receiving area 134 on an upper surface of each respective cover portion 78a, 78b. This receiving area 134 is configured to receive a bottom of at least one medical waste container 14 stacked or positioned thereon. For example, FIG. 8 illustrates a plurality of transport devices 10, loaded with containers 14, and stacked for transport on a dolly 138. The rib 130 and the associated receiving area 134 operate to position and retain the bottom of a container 14 stacked on the supporting cover portion. The rib 130 defines a raised perimeter that limits movement of the bottom of a stacked container 14.

Figure 3C:
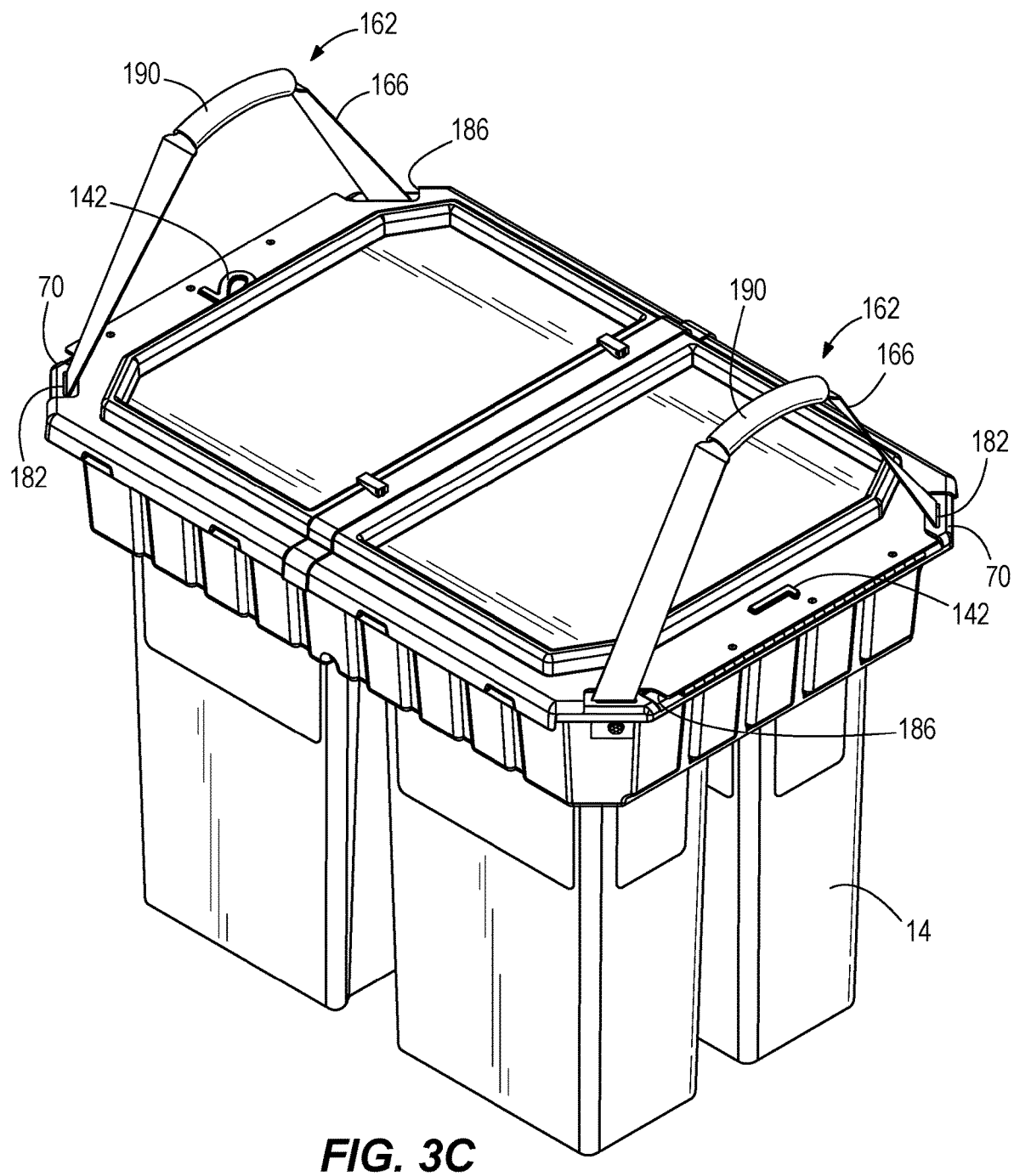
FIG. 3C is a perspective view of the transport device of FIG. 1 having optional cover indicia.

The illustrated transport device 10 further includes optional handles 162 configured to facilitate lifting and carrying the transport device 10 when loaded with containers 14. While various handle designs can be used, in the illustrated embodiment, each handle 162 includes a flexible strap 166 fastened at its ends to spaced-apart locations of the side wall 26. Fasteners 170 (see FIG. 1), which can include a nut 174 and bolt 178 as shown in FIG. 3A, or any other suitable fastener, pass through and secure the ends of the flexible strap 66 to the side wall 26. As best seen in FIG. 3C, the ends of the flexible strap 166 extend through respective apertures 182 in the flange 70 of the side wall 26. Cutouts 186 are provided in the first and second cover portions 78a, 78b to enable the cover portions 78a, 78b to pivot freely without being inhibited by the handles 162. A tubular hand-hold 190 is positioned on the flexible strap 166 to provide a comfortable grip for the user. The hand-hold 190 can be made of a soft, resilient material, providing a more comfortable grip than if the user were to grab the flexible strap 166 alone. While the flange 70 and lip 74 can provide a good gripping feature around the entire periphery of the device 10, the optional handles 162 improve the ease with which the device 10 can be lifted and transported.

When medical waste containers 14 are full and pickup is desired at a medical facility, a service technician can take one or more transport devices 10 to the medical facility. As shown in FIG. 4, a stack of transport devices 10 can be taken to the medical facility. FIGS. 9-13 illustrate the method of loading the transport device 10 for the transport of filled medical waste containers 14. With the filled waste containers 14 at hand, a single transport device 10 having the appropriate opening configuration for the particular filled containers 14 is selected and placed on the ground or a support surface (e.g., a table, or desk, or box). The cover portions 78a, 78b are opened so that the top of the cavity 42 is accessible for the insertion of the containers 14 (see FIG. 9). Next, the technician positions the bottom of each container 14 into a respective opening 30 in the base wall 22. The bottom of the containers 14 will actually be resting on the support surface, but the bottom of the containers 14 will be surrounded by the boundary portions 34 that define the openings 30 (see FIG. 10).

Figure 11:
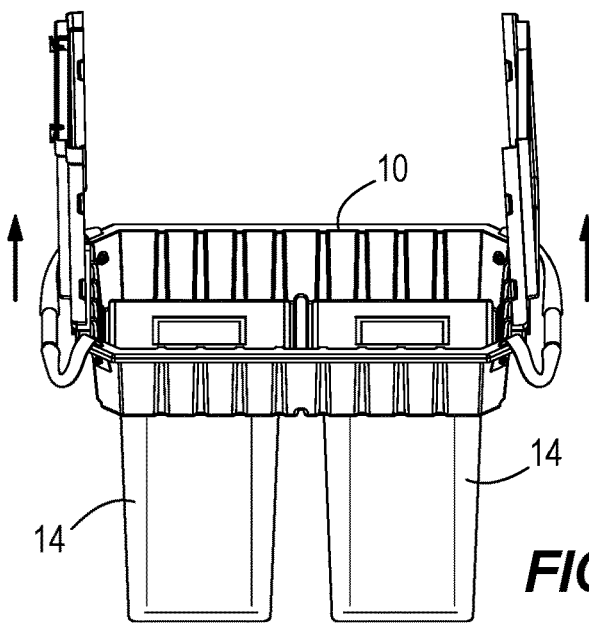

Next, the technician will move the transport device 10 upwardly relative to the containers 14 as shown in FIG. 11. This can be done by grasping and lifting the first and second cover portions 78a, 78b. Alternatively, the technician could lift the body 18 (e.g., at the flange 70, etc.) or the handles 162. The body 18 will move upwardly relative to the containers 14 until the respective boundary portions 34 engage the exterior surfaces of the respective containers 14. At this point, further upward movement of the transfer device 10 will result in the containers 14 being lifted off of the support surface as shown in FIG. 11. One or more quick upward thrusts of the transfer device 10 can facilitate obtaining a snug fit between the exterior of the containers 14 and the respective boundary portion 34.

Figure 12:
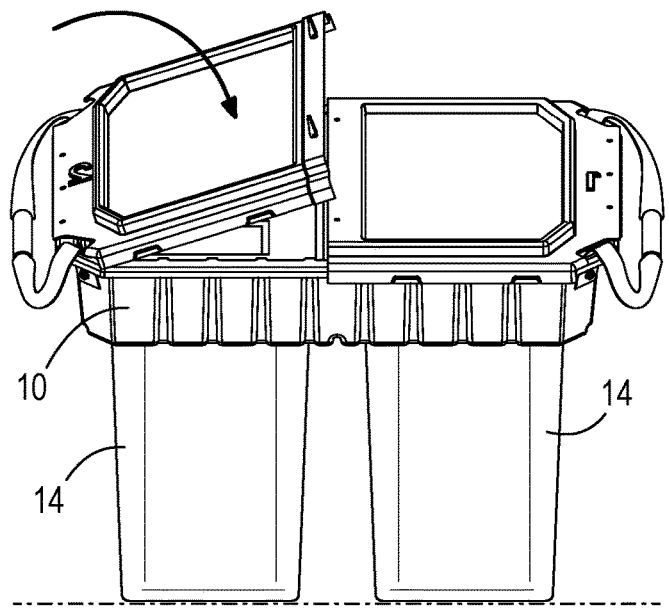

The technician can then set the transport device 10 and loaded containers 14 back on the support surface and close the first and second cover portions 78a, 78b (see FIG. 12). In the illustrated embodiment, the second cover portion 78b will be closed first and the first cover portion 78a will be closed second, due to the configurations of the overlapping and underlapping portions 122, 126 and the lock 102, to arrive at the closed position shown in FIGS. 1 and 13. The cover portions 78a, 78b can include indicia 142 thereon (see FIG. 3C—e.g., a number "1" and a number "2", or a letter "A" and a letter "B") to assist the technician in knowing which cover portion to close first and which to close second. The indicia can be configured and located to be highly visible on the cover portions 78a, 78b. As shown in FIGS. 3 and 3C, the indicia 142 can be molded directly into the plastic and are oriented in the proper viewing orientation when the cover portions 78a, 78b are in the open position, and are therefore in the backward or mirror orientation when the cover portions 78a, 78b are in the closed position.

Figure 5:
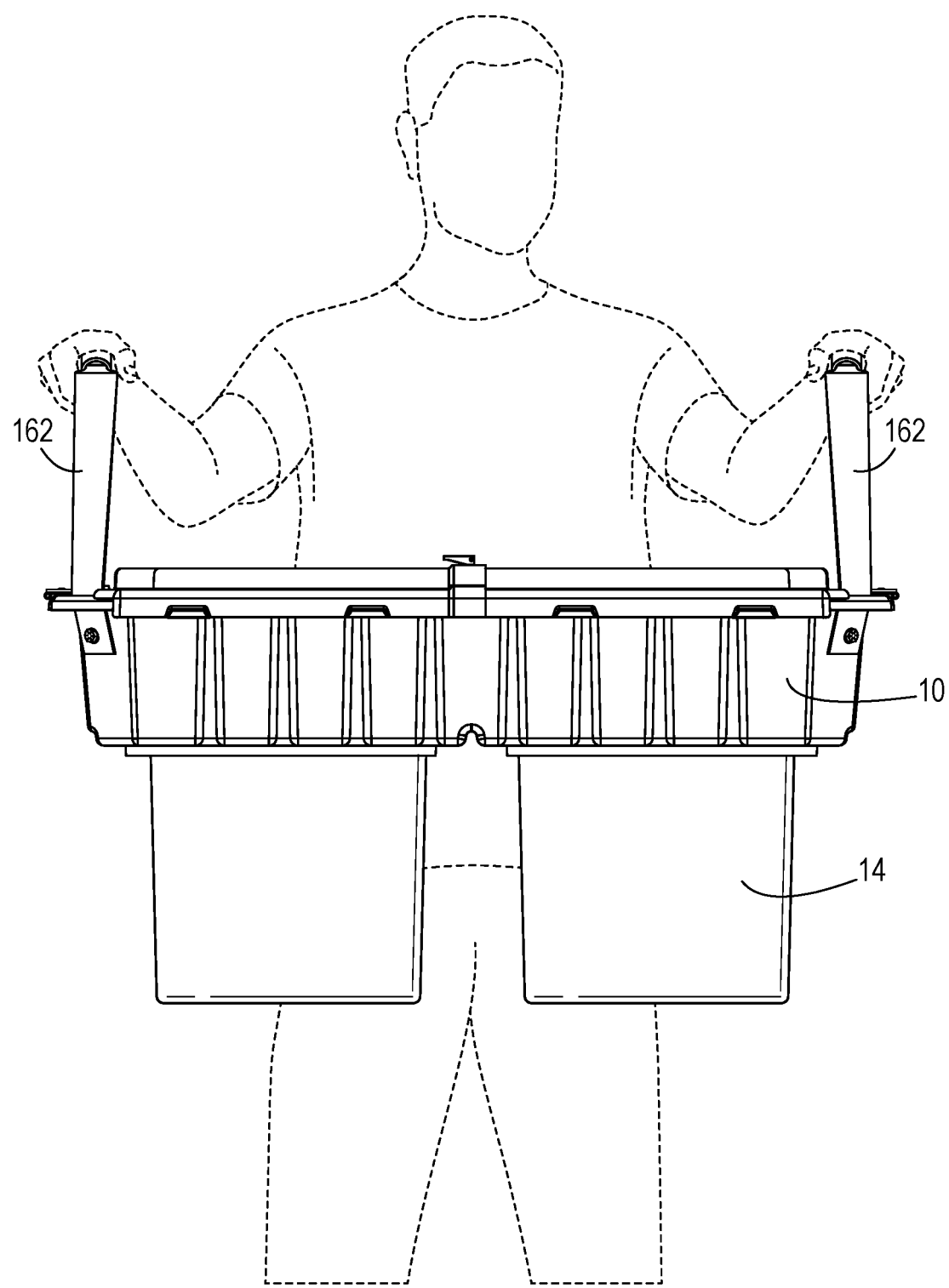
FIG. 5 illustrates the transport device of FIG. 1 loaded with medical waste containers and being carried by a service technician.
Figure 13:
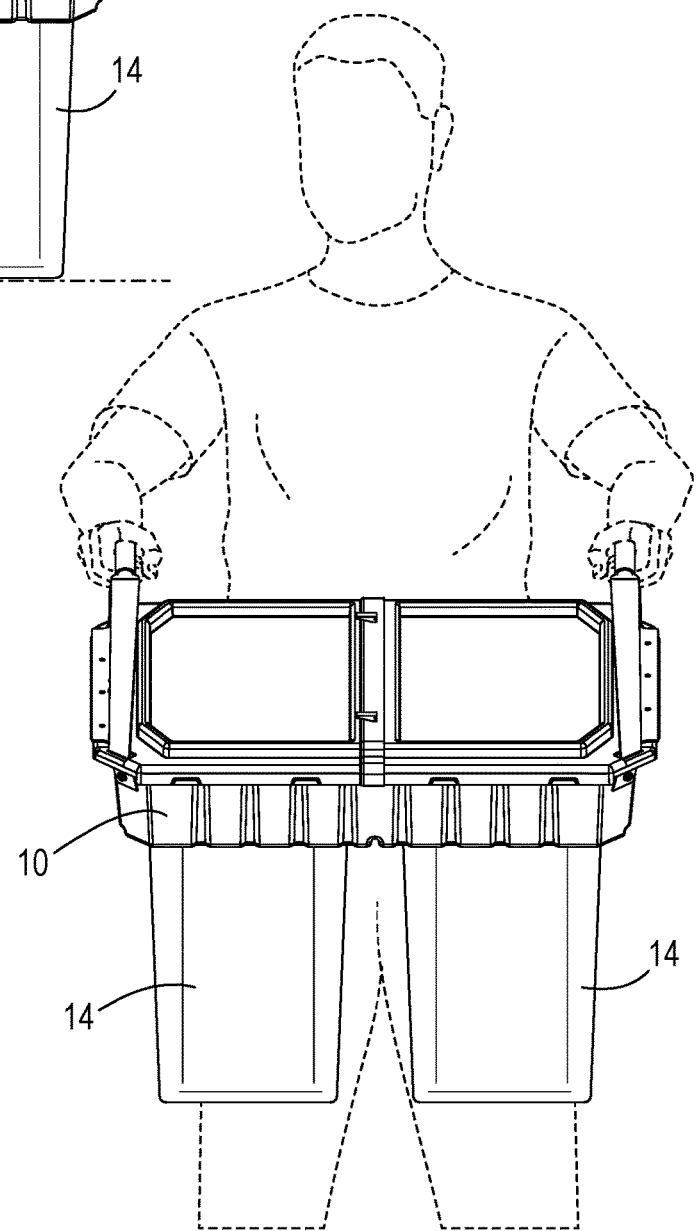

The projections 98 will all snap into place under the lip 74, and the lock(s) 102 can be manipulated to the secured/locked position. With the cover portions 78a, 78b closed and locked (i.e., secured closed) in this manner, the cavity 42 is completely closed in that the cover portions 78a, 78b close the top of the cavity 42 while the containers 14 plug or close off the openings 30. Access to the upper end of the containers 14, which contain the access points into the containers 14 and the closures or lids for those access points, is restricted because the upper ends of the containers 14 are completely enclosed within the cavity 42. In this condition, the transport device 10 is ready to be lifted and transported as shown in FIGS. 13, 5, and 8. The handles 162 facilitate the lifting and transportation. Alternatively, the flange 70 and lip 74 provide a good gripping feature around the entire periphery of the device 10.

The device 10 complies with the Department of Transportation's Hazardous Materials Regulations (HMR: 49 CFR Parts 171-180) relating to enclosures for transporting medical waste containers, and qualifies as an "overpack" under § 173.25, including the package marking and label visibility requirements. The device 10 ensures that while the containers 14 are loaded into the device 10 with the cover 78 closed, the individual sharps containers 14 remain fully closed and lidded. The individual containers 14 are prevented from tipping over and spilling in transit. As such, the device 10 may be used to transport sharps containers 14.

In the illustrated embodiment, at least seventy-five percent of the container's height extends from the underside of the transport device 10 so as to remain visible during transport. In other embodiments, and depending on the size of the containers 14, the percentage of exposed height of the containers can range from fifty percent to ninety-five percent. As such, the requisite markings and labels on the containers 14 remain visible during transport. This means that no markings or labels need be applied to the transport device 10 itself. As shown in FIG. 3B, approximately ¾ of the overall height of the lidded container extends from the underside of the device 10, while approximately ¼ of the overall height of the lidded container is fully enclosed within the device 10. This ratio can vary depending on the containers 14, however in each case, more of the overall container height is exposed outside of the device 10 than is enclosed within the device 10.

Removing the loaded containers 14 from the transfer device 10 occurs in the reverse manner. If the snug engagement between the boundary portions 34 and the exteriors of the containers 14 is tight, one or more quick downward thrusts of the body 18 when the containers are supported on a support surface and the cover 78 is open will release the containers 14 from within the openings 30. The body 18 can then be dropped downwardly to the supporting surface. The containers 14 can then be removed from within the cavity 42 for emptying and recycling. The transport device 10 is then ready for its next use and/or cleaning.

Although the invention has been described in detail with reference to certain preferred embodiments, variations and modifications exist within the scope and spirit of one or more independent aspects of the invention as described.

What is claimed is:

1. A transport device configured to removably receive a medical waste container for transport of the medical waste container, the transport device comprising:
   a body having
      a base wall with at least one opening for receiving a medical waste container, a portion of the base wall defining the at least one opening is configured to engage and completely surround an exterior of the medical waste container, and
      a side wall extending from the base wall, the base wall and side wall together defining a cavity; and
   a cover movably coupled to the side wall;
   wherein the cover is movable between a closed position, in which the cover cooperates with the side wall to close a top of the cavity, and an open position, in which the cavity is open at the top.

2. The transport device of claim 1, wherein the cover is pivotably coupled to the side wall for movement between the closed position and the open position.

3. The transport device of claim 1, wherein the cover comprises:
   a first cover movably coupled to the side wall; and
   a second cover movably coupled to the side wall;
   wherein each of the first and second covers are movable between the closed position, in which the first and second covers cooperate with the side wall to close the top of the cavity, and the open position, in which the cavity is open at the top.

4. The transport device of claim 3, wherein the first cover is pivotably coupled to a first portion of the side wall and the second cover is pivotably coupled to a second portion of the side wall.

5. The transport device of claim 4, wherein the first and second portions of the side wall are on opposite sides of the cavity.

6. The transport device of claim 3, further comprising a lock cooperating with the first and second covers to selectively secure the first and second covers in the closed position.

7. The transport device of claim 1, further comprising a lock coupled with the cover to secure the cover in the closed position.

8. The transport device of claim 1, wherein the cover includes projections that cooperate with the side wall to releasably maintain the cover in the closed position.

9. The transport device of claim 8, wherein the side wall includes a flange at an upper end of the side wall, the flange having a downwardly extending lip, and wherein the projections on the cover engage the downwardly extending lip to releasably maintain the cover in the closed position.

10. The transport device of claim 1, wherein the base wall includes two openings, four openings, or six openings.

11. The transport device of claim 1, wherein the cover includes a rib that defines a receiving area on the cover to receive a bottom portion of at least one medical waste container.

12. The transport device of claim 1, wherein the side wall is formed with a draft angle such that the cavity tapers from a narrower dimension adjacent the base wall to a wider dimension adjacent the top of the cavity.

13. The transport device of claim 1, wherein the side wall is rectangular and includes ribbing on an interior surface defining the cavity.

14. The transport device of claim 1, further comprising first and second handles coupled to the body.

15. The transport device of claim 14, wherein each of the first and second handles includes a flexible strap fastened to the side wall.

16. The transport device of claim 15, wherein the flexible strap extends through an aperture in a flange of the side wall.

17. A method of using the transport device of claim 1, the method comprising:
   placing the transport device on a support surface with the base wall on the support surface;
   moving the cover to the open position such that the cavity is open at the top;
   placing the medical waste container through the open top of the cavity into the cavity so that a bottom of the medical waste container is positioned in the at least one opening and on the support surface;
   moving the transport device relative to the medical waste container toward a top of the medical waste container until an exterior of the medical waste container engages a portion of the base wall defining the at least one opening; and
   moving the cover to the closed position so that an upper end of the medical waste container is enclosed within the closed cavity of the transport device.

18. The method of claim 17, wherein the transport device is a first transport device and the medical waste container is a first medical waste container further comprising:
   stacking a second transport device holding a second medical waste container on top of the first transport device, the cover of the first transport device including a raised rib that defines a receiving area on the cover to receive a bottom portion of the second medical waste container that is held by the second transport device.

19. The method of claim 17, wherein the transport device includes a first cover movably coupled to the side wall, and a second cover movably coupled to the side wall, wherein each of the first and second covers are movable between the closed position, in which the first and second covers cooperate with the side wall to close the top of the cavity, and the open position, in which the cavity is open at the top; and
   wherein moving the cover to the open position includes moving both of the first and second covers to the open position; and
   wherein moving the cover to the closed position includes moving both of the first and second covers to the closed position.

20. The method of claim 19, wherein moving the first and second covers includes pivoting the covers.

21. The method of claim 17, further comprising:
   locking the cover in the closed position.

22. The method of claim 17, wherein moving the cover to the closed position includes resiliently engaging projections on the cover with mating engagement features on the side wall.

* * * * *